(12) United States Patent
Imada

(10) Patent No.: US 9,065,057 B2
(45) Date of Patent: Jun. 23, 2015

(54) ARYL-AMINE DERIVATIVE AND ORGANIC ELECTROLUMINESCENT DEVICE USING THE SAME AS A HOLE TRANSPORT MATERIAL

(71) Applicant: SAMSUNG DISPLAY CO., LTD., Yongin, Gyeonggi-Do (KR)

(72) Inventor: Ichiro Imada, Yokohama (JP)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 0 days.

(21) Appl. No.: 14/284,874

(22) Filed: May 22, 2014

(65) Prior Publication Data

US 2014/0350247 A1    Nov. 27, 2014

(30) Foreign Application Priority Data

May 24, 2013    (JP) .................................. 2013-109921

(51) Int. Cl.

| | | |
|---|---|---|
| C07D 401/14 | (2006.01) | |
| C07D 401/12 | (2006.01) | |
| C07D 403/14 | (2006.01) | |
| C07D 403/12 | (2006.01) | |
| H01L 51/52 | (2006.01) | |
| H01L 51/54 | (2006.01) | |
| H01L 51/00 | (2006.01) | |
| H01L 51/50 | (2006.01) | |

(52) U.S. Cl.
CPC ........ H01L 51/0052 (2013.01); H01L 51/0061 (2013.01); H01L 51/0072 (2013.01); H01L 51/0067 (2013.01); H01L 51/0073 (2013.01); H01L 51/006 (2013.01); C07D 403/12 (2013.01); H01L 51/5032 (2013.01); H01L 51/5064 (2013.01); C07D 401/12 (2013.01); C07D 403/14 (2013.01); C07D 401/14 (2013.01); H01L 51/0032 (2013.01)

(58) Field of Classification Search
CPC .. C07D 401/14; C07D 401/12; C07D 403/14; C07D 403/12; H01L 51/0032; H01L 51/5032; H01L 51/5064
USPC ........... 428/917; 548/444; 544/194, 323, 326; 546/276.4
See application file for complete search history.

(56) References Cited

U.S. PATENT DOCUMENTS

| | | | |
|---|---|---|---|
| 8,685,542 B2 | 4/2014 | Kim et al. | |
| 8,795,852 B2 * | 8/2014 | Asari et al. | ..................... 428/690 |
| 8,808,874 B2 * | 8/2014 | Otsu et al. | ..................... 428/690 |
| 2007/0149784 A1 * | 6/2007 | Murata et al. | ................. 548/143 |

FOREIGN PATENT DOCUMENTS

| | | |
|---|---|---|
| CN | 101161765 A | 4/2008 |
| EP | 0-906-948 A1 | 4/1999 |
| EP | 2-371-828 A1 | 10/2011 |
| JP | 2004-214050 A | 7/2004 |
| JP | 2010-527923 A | 8/2010 |
| KR | 10-2010-0131745 A | 12/2010 |
| KR | 10-2011-0079402 A | 7/2011 |
| KR | 10-2012-0009984 A | 2/2012 |
| KR | 10-2012-0092909 A | 8/2012 |
| WO | WO-2009-008344 A1 | 1/2009 |
| WO | WO 2011/059099 A1 | 5/2011 |
| WO | WO-2012-015265 A | 2/2012 |
| WO | WO 2012/077902 A2 | 6/2012 |
| WO | WO-2012-091471 A2 | 7/2012 |

* cited by examiner

*Primary Examiner* — Venkataraman Balasubramanian
(74) *Attorney, Agent, or Firm* — Lee & Morse, P.C.

(57) ABSTRACT

An aryl amine derivative and an organic electroluminescent device using the aryl amine derivative as a hole transport material, the aryl amine derivative being represented by the following Chemical Formula 1.

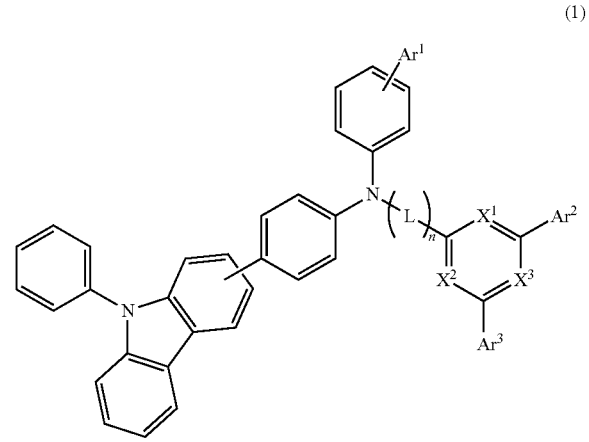

(1)

7 Claims, 1 Drawing Sheet

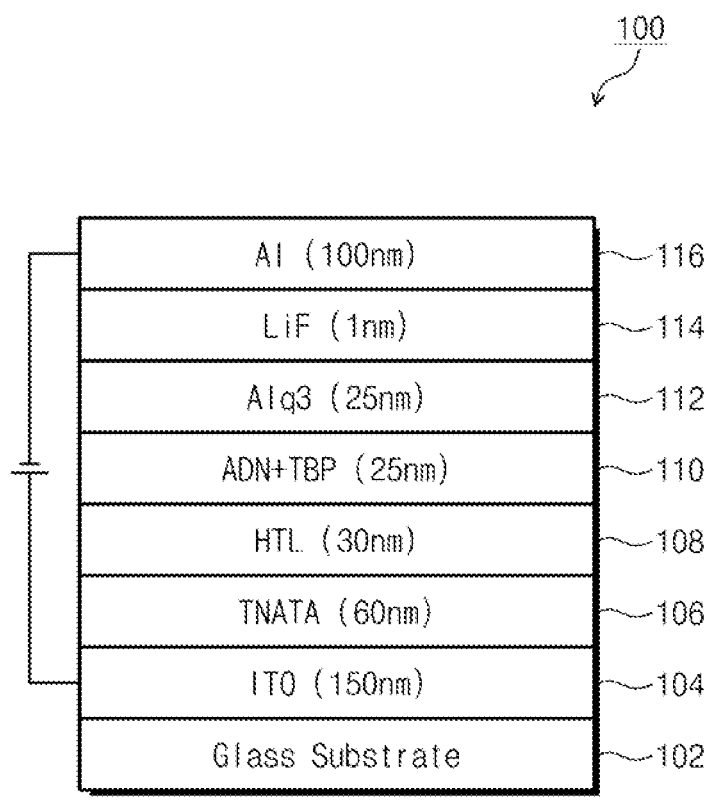

ARYL-AMINE DERIVATIVE AND ORGANIC ELECTROLUMINESCENT DEVICE USING THE SAME AS A HOLE TRANSPORT MATERIAL

CROSS-REFERENCE TO RELATED APPLICATION

Japanese Patent Application No. 2013-109921, filed on May 24, 2013, in the Japanese Intellectual Property Office, and entitled: "Aryl-Amine Derivative And Organic Electroluminescent Device Using The Same As Hole Transport Material," which is incorporated by reference herein in its entirety.

BACKGROUND

1. Field

Embodiments relate to an aryl amine derivative and an organic electroluminescent device using the same as a hole transport material.

2. Description of the Related Art

Organic electroluminescence display apparatuses (organic EL display apparatuses) have been developed as image display devices. The organic EL display apparatus is a self-luminous display device, unlike a liquid crystal display apparatus. For example, holes and electrons from an anode and a cathode may be recombined with each other in a light-emitting layer of the organic EL display apparatus, and an organic light-emitting material included in the light-emitting layer emits light to display an image.

An organic electroluminescent device (organic EL device) may include, e.g., an anode, a hole transport layer on the anode, a light-emitting layer on the hole transport layer, an electron transport layer on the light-emitting layer, and a cathode on the electron transport layer. Holes may be injected from the anode, and the injected holes may be provided into the light-emitting layer through the hole transport layer. Electrons may be injected from the cathode, and the injected electrons may be provided into the light-emitting layer through the electron transport layer. The holes and electrons provided into the light-emitting layer may be recombined with each other to generate excitons in the light-emitting layer. The organic EL device may emit light using light generated by radiation deactivation of the excitons. However, the structure of the organic EL may be variously modified.

SUMMARY

Embodiments are directed to an aryl amine derivative and an organic electroluminescent device using the same as a hole transport material.

The embodiments may be realized by providing an aryl amine derivative represented by the following Chemical Formula 1,

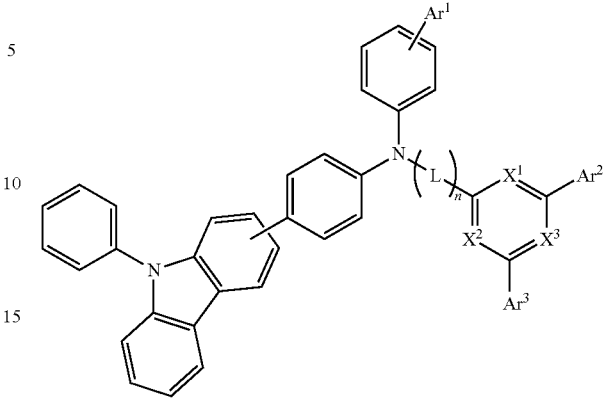

(1)

wherein, in Chemical Formula 1 $Ar^1$, $Ar^2$, and $Ar^3$ are each independently a substitutable aryl group or a substitutable heteroaryl group, L is a single bond, a substitutable C6 to C25 arylene group, or a substitutable C5 to C25 heteroarylene group, n is an integer of 1 to 3, $X^1$, $X^2$, and $X^3$ are each independently a carbon atom or a nitrogen atom, provided that at least one of $X^1$, $X^2$, or $X^3$ is a nitrogen atom.

$X^1$, $X^2$, and $X^3$ may be nitrogen atoms.

$Ar^2$ and $Ar^3$ may be different from each other.

The embodiments may be realized by providing an organic electroluminescent device including a hole transport layer including an aryl amine derivative represented by the following Chemical Formula 1,

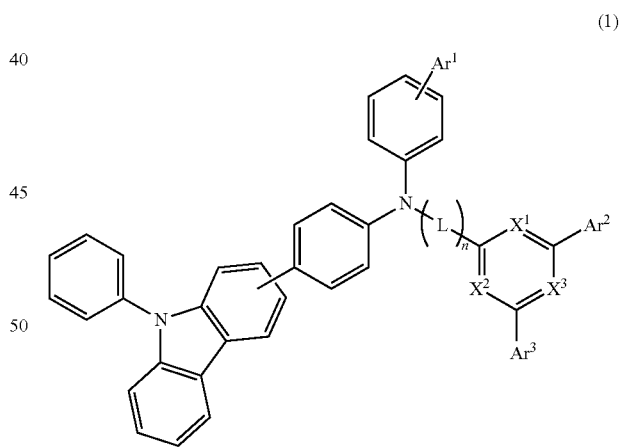

(1)

wherein, in Chemical Formula 1 $Ar^1$, $Ar^2$, and $Ar^3$ are each independently a substitutable aryl group or a substitutable heteroaryl group, L is a single bond, a substitutable C6 to C25 arylene group, or a substitutable C5 to C25 heteroarylene group, n is an integer of 1 to 3, $X^1$, $X^2$, and $X^3$ are each independently a carbon atom or a nitrogen atom, provided that at least one of $X^1$, $X^2$, or $X^3$ is a nitrogen atom.

$X^1$, $X^2$, and $X^3$ may be nitrogen atoms.

$Ar^2$ and $Ar^3$ may be different from each other.

BRIEF DESCRIPTION OF THE DRAWING

Features will be apparent to those of skill in the art by describing in detail exemplary embodiments with reference to the attached drawing in which:

FIG. 1 illustrates a schematic diagram of an organic electroluminescent device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

According to an embodiment, an azine group (e.g., an electron transport material or group) may be included on an aryl amine derivative, and durability of a hole transport layer with respect to electrons may be improved. An organic electroluminescent device with high efficiency and long lifetime may be realized. An azine group may refer to a six-membered heterocyclic compound that contains one or more atoms of nitrogen in the ring structure and may not include a nitrogen-nitrogen bond.

An aryl amine derivative and an organic electroluminescent device using the same according to an embodiment will be described hereinafter.

An aryl amine derivative according to an embodiment may be represented by the following Chemical Formula 1.

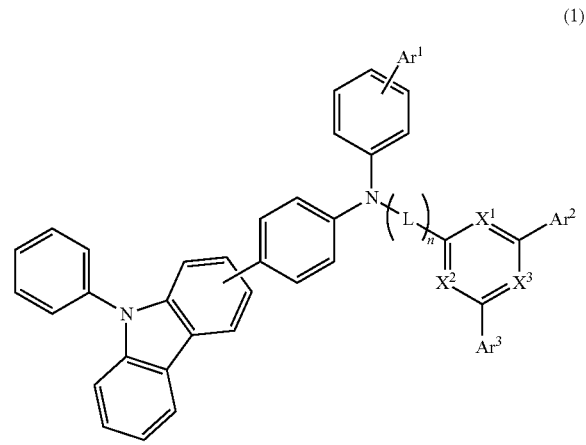

(1)

In Chemical Formula 1, $Ar^1$, $Ar^2$, and $Ar^3$ may be different from or the same as each other. For example, $Ar^1$, $Ar^2$, and $Ar^3$ may be each independently a substitutable aryl group or a substitutable heteroaryl group (e.g., a substituted or unsubstituted aryl group or a substituted or unsubstituted heteroaryl group). L may be, e.g., a single bond, a substitutable C6 to C25 arylene group, or a substitutable C5 to C25 heteroarylene group (e.g., a substituted or unsubstituted C6 to C25 arylene group or a substituted or unsubstituted C5 to C25 heteroarylene group). n may be an integer of 1 to 3. $X^1$, $X^2$, and $X^3$ may each independently be a carbon atom or a nitrogen atom. In an implementation, at least one of $X^1$, $X^2$, or $X^3$ may be a nitrogen atom.

The azine group may be included on an aryl amine core or skeleton that also include a carbazole moiety. Thus, electron affinity of the aryl amine derivative may be improved, and the aryl amine derivative may not be used for emitting light. In addition, it is possible to help improve the durability of the aryl amine derivative with respect to electrons reaching a hole transport layer, e.g., the aryl amine derivative according to an embodiment may exhibit electron blocking properties. As a result, in the event that the aryl amine derivative according to an embodiment is used as or in the hole transport layer, durability of the hole transport layer to electrons may be improved, and a high-efficiency and long-life organic electroluminescent device may be fabricated. As described above, the embodiments may provide a compound including the azine group on the aryl amine core (that also includes a carbazole moiety bound thereto).

In the aryl amine derivative according to an embodiment, at least one of $X^1$, $X^2$, or $X^3$ may be a nitrogen atom. In an implementation, all of $X^1$, $X^2$, and $X^3$ may be nitrogen atoms. In an implementation, a number of nitrogen atom may be increased in the aryl amine derivative, and stability of the hole transport layer to the electrons may be improved. Thus, the aryl amine derivative according to an embodiment may be suitable to use during fabrication of organic electroluminescent devices.

In an implementation, $Ar^2$ and $Ar^3$ may be the same as or different from each other in the aryl amine derivative. For example, $Ar^2$ and $Ar^3$ may be different from each other. In the aryl amine derivative according to an embodiment, functional groups having different structures from each other may be introduced onto the aryl amine skeleton (that also includes a carbazole moiety bonded thereto). The azine group may have low symmetry as a molecule, but may cause a stack of molecules due to a structure of the azine group. As noted above, $Ar^2$ and $Ar^3$ may be different from each other, and the stacking of molecules (which may otherwise occur due to the inclusion of the azine group) may be inhibited, and a highly-amorphous hole transport material may be realized.

In the aryl amine derivative according to an embodiment, $Ar^1$, $Ar^2$, and $Ar^3$ may be different from or the same as each other. In an implementation, $Ar^1$, $Ar^2$, and $Ar^3$ may each independently be a substitutable aryl group or a substitutable hetero-aryl group (e.g., a substituted or unsubstituted aryl group or a substituted or unsubstituted heteroaryl group). In an implementation, one of $Ar^1$, $Ar^2$, or $Ar^3$ may have a carbon number of 10 or more. In an implementation, one of $Ar^1$, $Ar^2$, or $Ar^3$ may be a naphthyl group.

As noted above, in the aryl amine derivative according to an embodiment, L may be, e.g., a single bond, a substitutable C6 to C25 arylene group, or a substitutable C5 to C25 heteroarylene group (e.g., a substituted or unsubstituted C6 to C25 arylene group or a substituted or unsubstituted C5 to C25 heteroarylene group). As noted above, n may be an integer of 1 to 3. Maintaining a number of atoms that form the ring of the arylene group or heteroarylene group at 25 or fewer may help ensure that a size of the aryl amine derivative is not excessively increased. Thus, the aryl amine derivative may be suitably used as the hole transport material.

In an implementation, the aryl amine derivative according to an embodiment, e.g., the aryl amine derivative represented by Chemical Formula 1 may include one of the following Compounds 4-9.

(4)
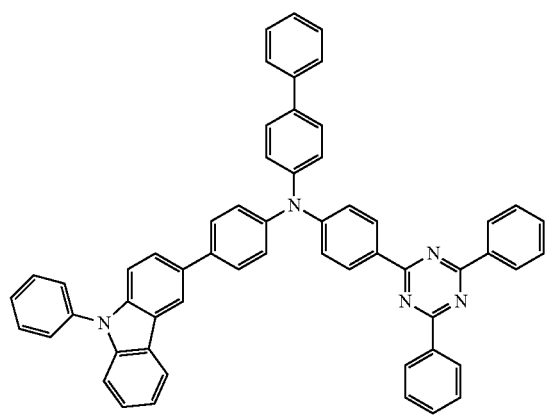
(5)
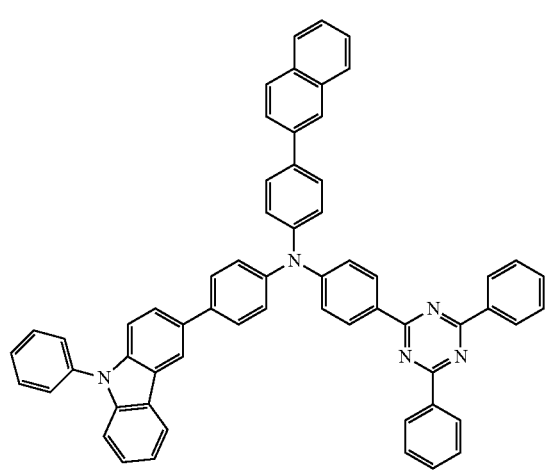
(6)
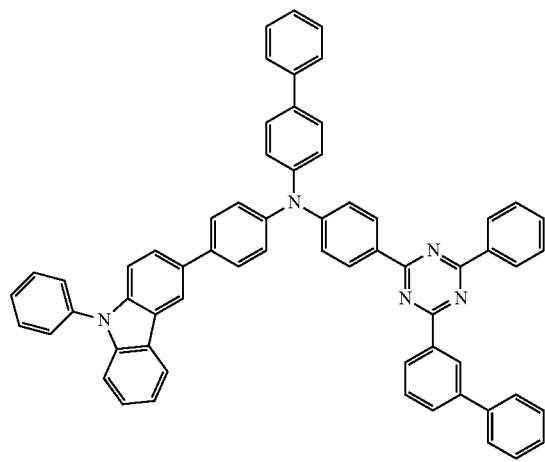
(7)
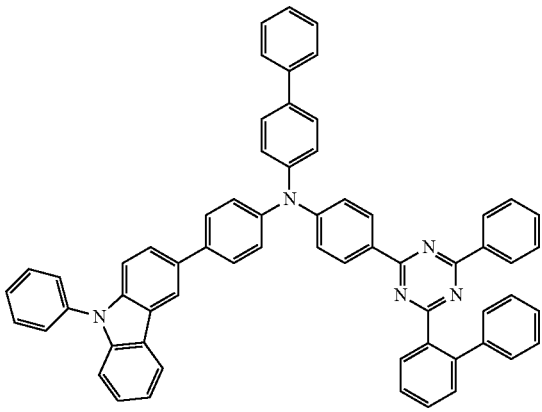
(8)
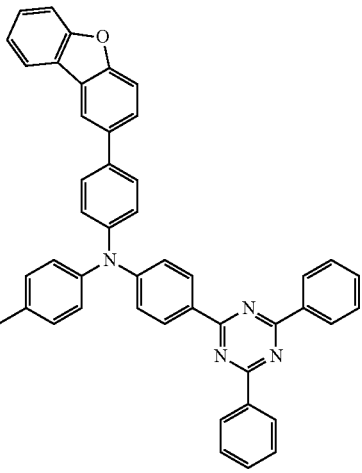
(9)
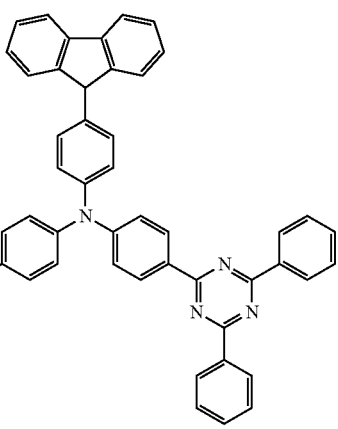
In an implementation, the aryl amine derivative according to an embodiment, e.g., the aryl amine derivative represented by Chemical Formula 1 may include one of the following Compounds 10-15.

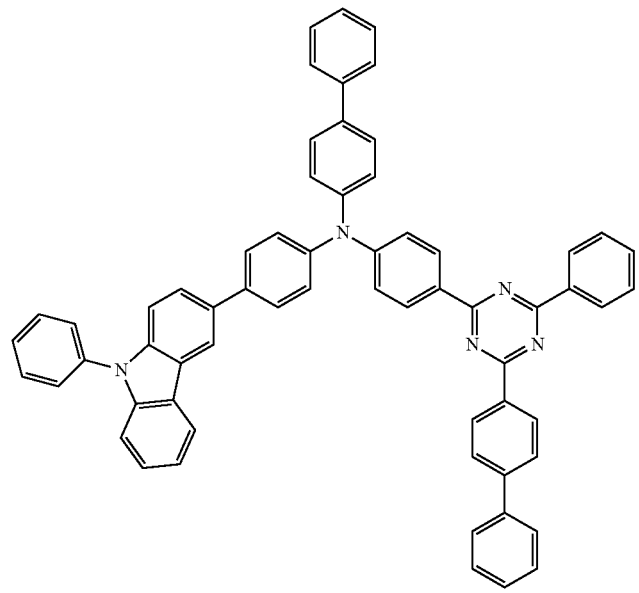
(10)
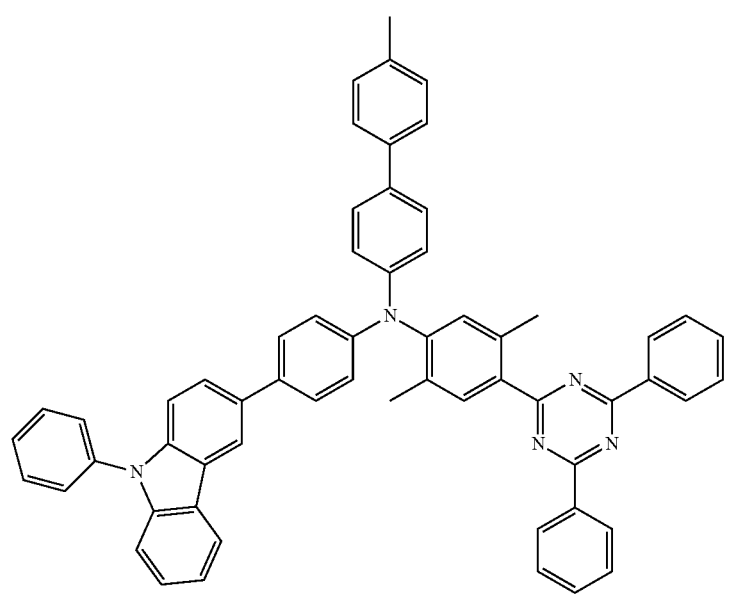
(11)

(12)
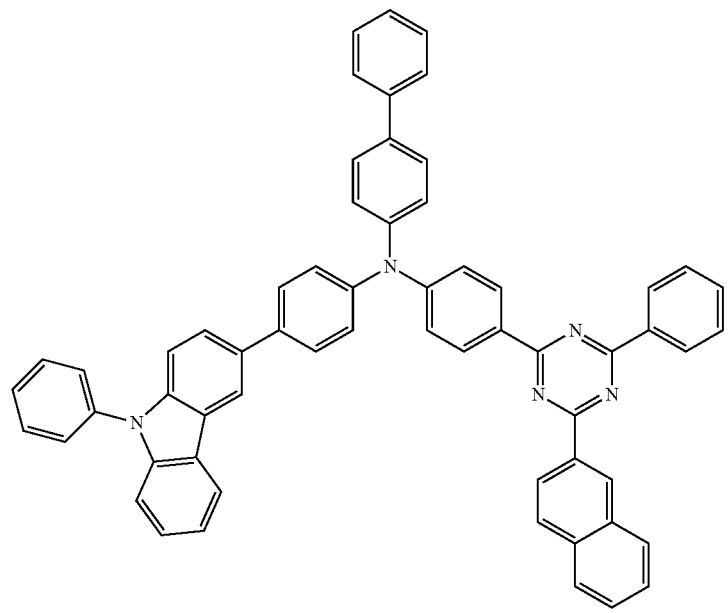
(13)
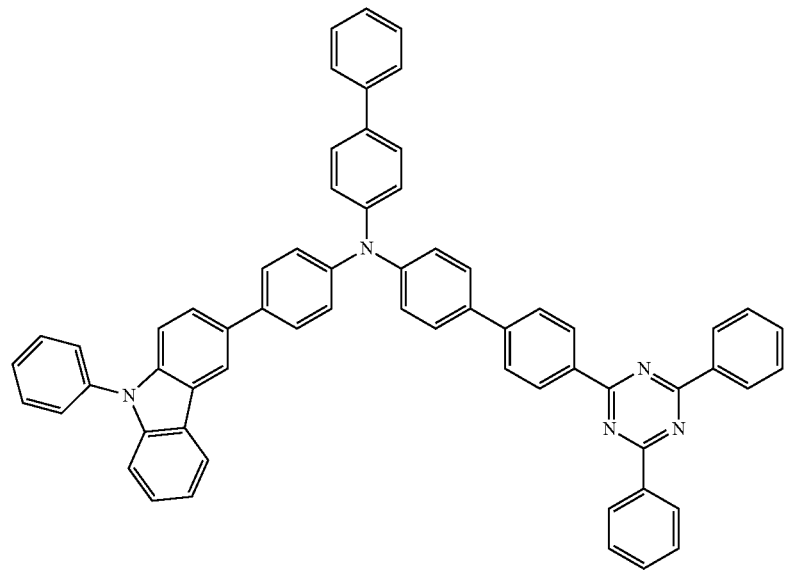

(14)
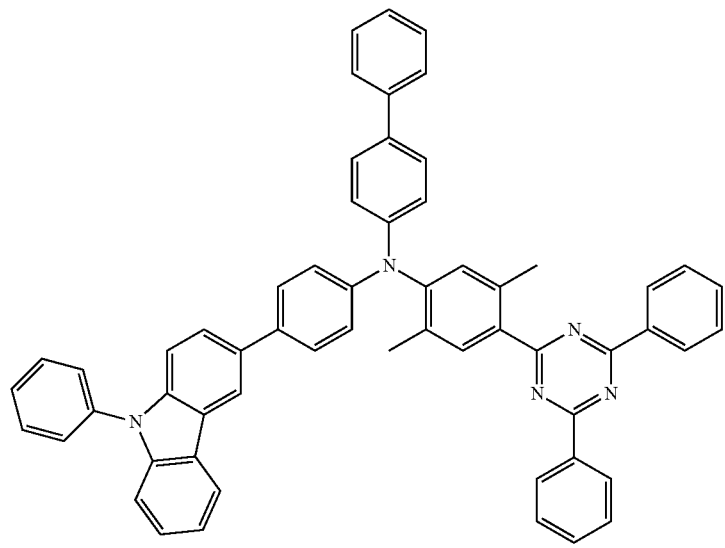
(15)
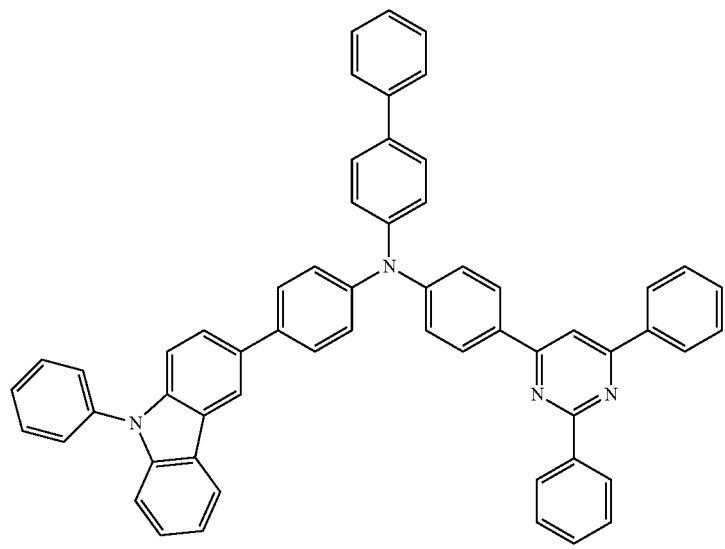
In an implementation, aryl amine derivative according to an embodiment, e.g., the aryl amine derivative represented by Chemical Formula 1 may include one of the following Compounds 16-21.
(16)
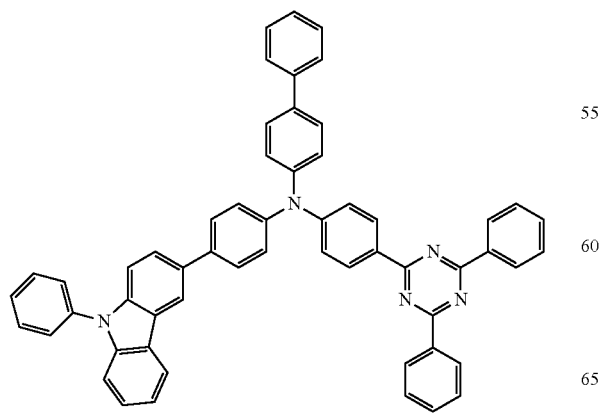
(17)
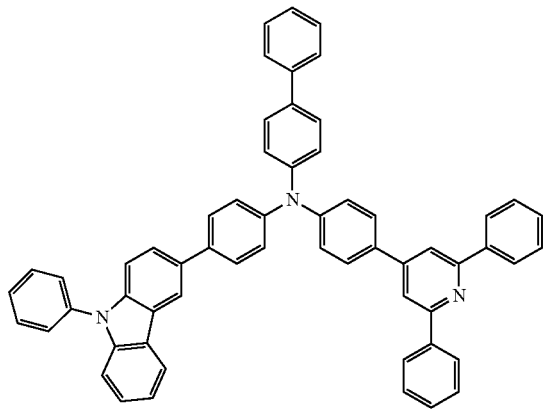

(18)
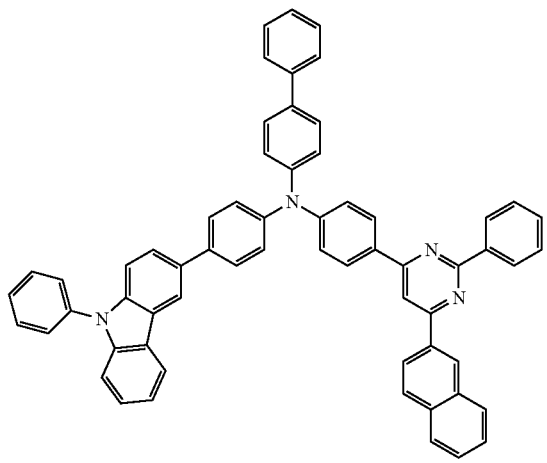

(21)
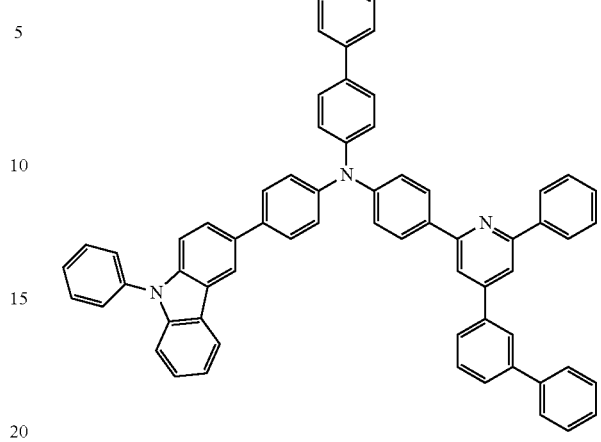

(19)
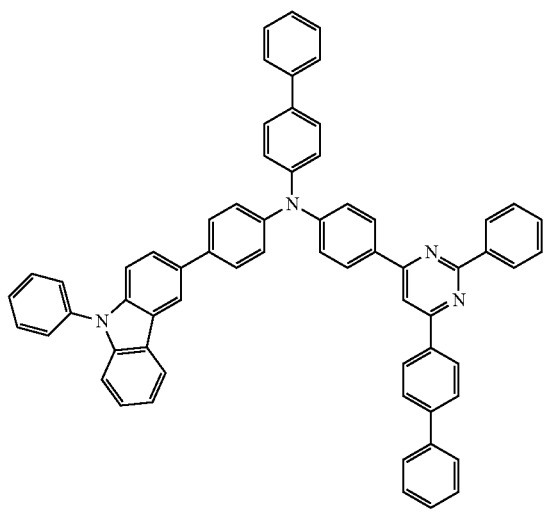

(20)
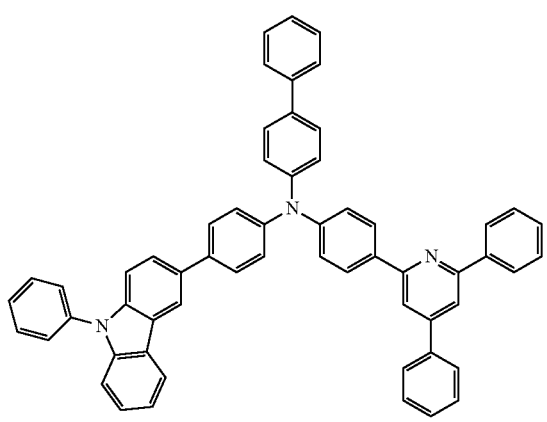

The aryl amine derivative according to an embodiment may have at least one of the chemical structures described above, and thus, a high-efficiency and long-lifetime hole transport layer may be provided in the organic electroluminescent device. The aryl amine derivative according to an embodiment may include the carbazole moiety, and a charge transporting property of the aryl amine derivative may be improved, and a low-voltage organic electroluminescent device may be realized. In addition, the azine group may be included in the aryl amine derivative according to an embodiment, and the aryl amine derivative may not be used as a light-emitting layer. In addition, it is possible to help improve a resistance property of the aryl amine derivative with respect to electrons invading the hole transport layer and a lifetime of the aryl amine derivative. Furthermore, the aryl amine derivative according to an embodiment may have the structures described above, so the high-efficiency and long-lifetime organic electroluminescent device may be realized.

[Organic Electroluminescent Device]

An organic electroluminescent device using the aryl amine derivative according to an embodiment as a hole transport material will be described hereinafter. FIG. 1 illustrates a schematic diagram of an organic electroluminescent device 100 according to an embodiment. The organic electroluminescent device 100 may include, e.g., a substrate 102, an anode 104, a hole injection layer 106, a hole transport layer 108, a light-emitting layer 110, an electron transport layer 112, an electron injection layer 114, and a cathode 116.

For example, the substrate 102 may be a transparent glass substrate, a semiconductor substrate formed of silicon, or a flexible substrate formed of resin. A method of forming an organic thin layer may include a suitable method, e.g., a general vacuum deposition method. In an implementation, the method of forming the organic thin layer may use at least one of various coating or applying formation methods. The anode 104 may be on the substrate 102 and may be formed of or may include, e.g., indium-tin oxide (ITO) or indium-zinc oxide (IZO). The hole injection layer 106 may be on the anode 104 and may include, e.g., 4,4',4''-tris(N-1-naphthyl-N-phenylamino)triphenylamine (1-TNATA) or 4,4'-Bis(N,N-di(3-tolyl)amino)-3,3-dimethylbiphenyl (HMTPD). The hole transport layer 108 may be on the hole injection layer 106 and may be formed of or may include the aryl amine derivative according to an embodiment. The light-emitting layer 110 may be on the hole transport layer 108 and may be formed by doping a host material including, e.g., 9,10-di-(2-naphthyl)anthracene (ADN) with tetra-t-butylperylene (TBP). The electron transport layer 112 may be on the light-emitting layer 110 and may be formed of or may include, e.g., tris(8-hydroxyquinolinato)aluminum ($Alq_3$). The electron injection layer 114 may be on the electron transport layer 112 and may be formed of or may include, e.g., lithium fluoride (LiF). The cathode 116 may be on the electron injection layer 114 and may be formed of or may include a metal (e.g., aluminum (Al)) or a transparent material (e.g., indium-tin oxide (ITO) or indium-zinc oxide (IZO)). Each of the thin layers may be formed by, e.g., a vacuum deposition method, a sputtering method, or at least one of various coating methods.

In the organic electroluminescent device 100 according to the present embodiment, the hole transport material including the aryl amine derivative described above may be used to form the hole transport layer that has high efficiency and a long lifetime. In an implementation, the hole transport material may also be applied to an organic electroluminescent device having an active matrix using thin film transistors (TFT).

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Embodiment

Fabricating Method

An aryl amine derivative according to an embodiment may be synthesized by the following method.

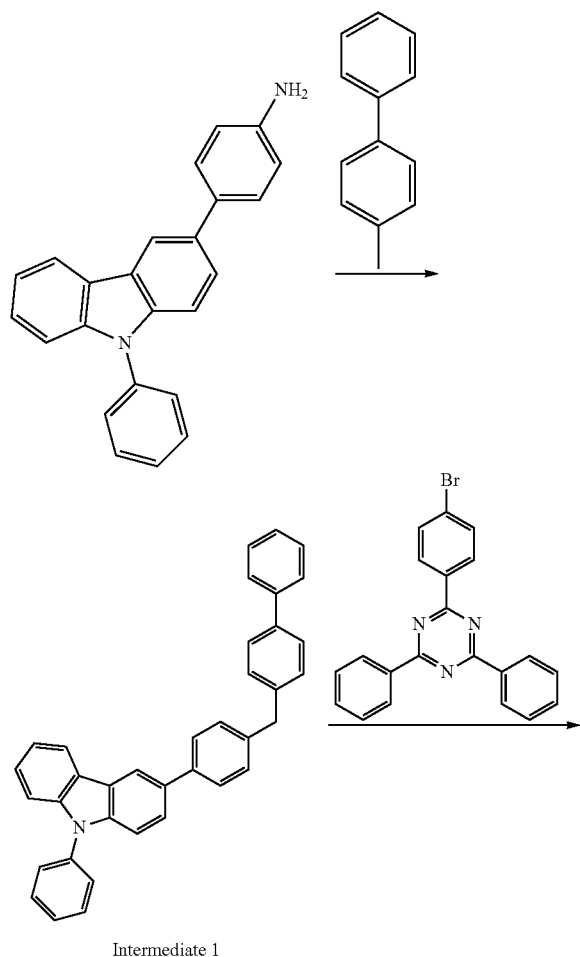

Intermediate 1

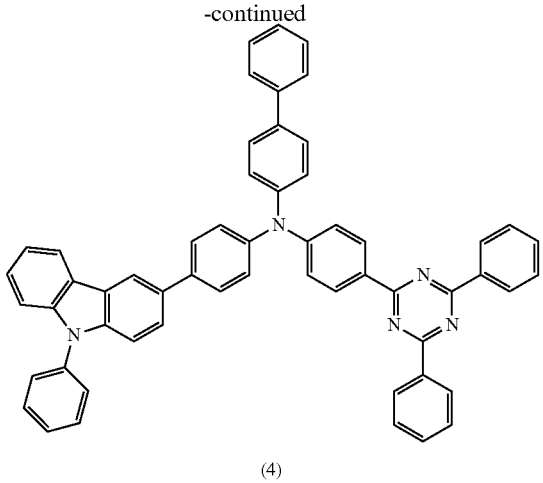

(4)

(Synthesis of Intermediate 1)

4-(9-phenyl-9H-carbazol-3-yl)aniline (3.0 g, 8.97 mmol), 4-iodobiphenyl (2.51 g, 8.97 mmol), and sodium-t-butoxide (1.2 g, 13.5 mmol) were added into a reaction container on which a nitrogen substitution process was performed, and toluene (600 mL) was added as a solvent into the reaction container. Next, a tris(tert-butylphosphine)toluene solution (P(t-Bu)$_3$tol.sol) (0.26 g, 0.27 mmol) and tris(dibenzylideneacetone)dipalladium(0) (Pd$_2$(dba)$_3$) (0.25 g, 0.45 mmol) were added, an inside of the container was substituted with nitrogen, and a solution in the container was stirred for six hours. The reaction solution was diluted with toluene (100 mL). The diluted reaction solution was filtered using Celite, and then, the filtered reaction solution was cleaned using a saturated saline solution to obtain an organic layer. The obtained organic layer was dried using anhydrous magnesium sulfate and then was filtered. A filtrate was concentrated by a rotary evaporator. An obtained crude product was refined by a silica gel chromatography, and an obtained solid was recrystallized to form 2.9 g of Intermediate 1. A yield of the obtained Intermediate 1 was 67%.

(Synthesis of Compound 4)

The same reaction as the synthesis of the Intermediate 1 was performed to the Intermediate 1 (1.2 g, 2.47 mmol) and 2-(4-bromophenyl)-4,6-diphenyl-1,3,5-triazine (1.05 g, 2.71 mmol) to obtain 1.2 g of Compound 4. A yield of the Compound 4 was 64%.

The synthesized compound was identified by a mass spectrum measurement method.

An Embodiment 1 (e.g., Compound 4), below, was obtained using the fabricating method described above. In addition, Comparison Examples 1, 2, and 3 were prepared.

Embodiment 1

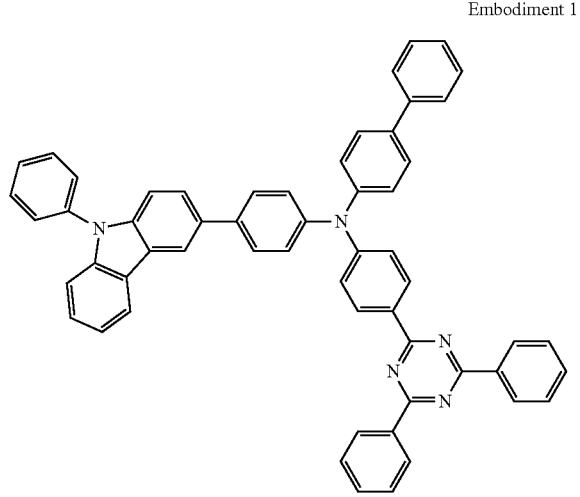

Comparison example 1

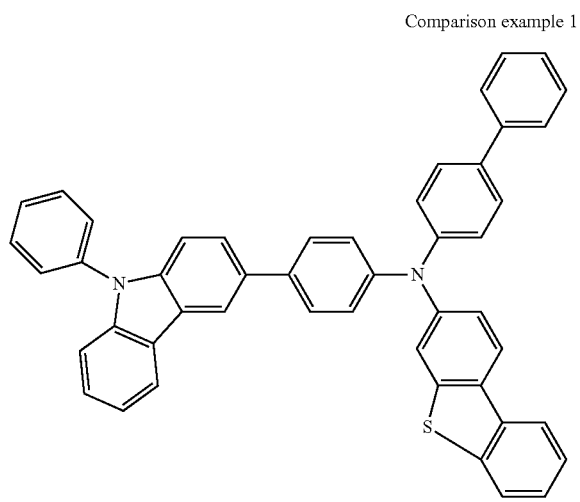

Comparison example 2

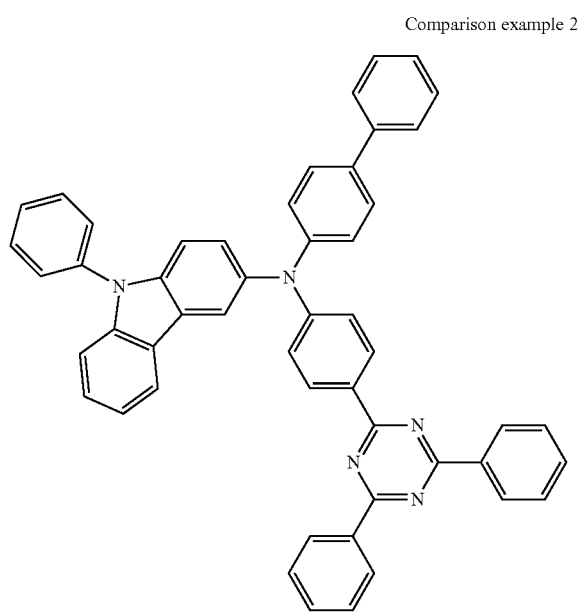

-continued

Comparison example 3

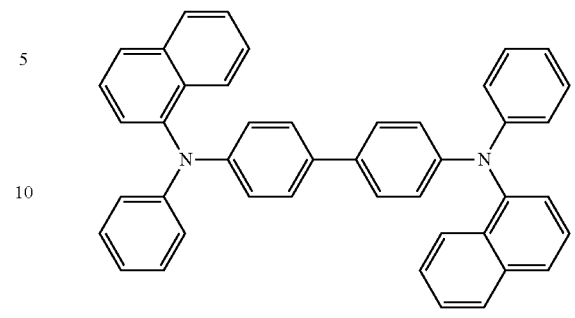

Organic electroluminescent devices described above were formed using Embodiment 1 and Comparison Examples 1 to 3 as hole transport materials. For example, a transparent glass substrate was used as the substrate 102, and the anode 104 was formed of ITO having a thickness of 150 nm. The hole injection layer 106 was formed of 1-TNATA having a thickness of 60 nm, and the hole transport layer 108 was formed (using Embodiment 1 or Comparison Examples 1, 2, or 3) to have a thickness of 30 nm. The light-emitting layer 110 was formed of ADN doped with 3% of TBP. The light-emitting layer 110 had a thickness of 25 nm. The electron transport layer 112 was formed of $Alq_3$ having a thickness of 30 nm, and the electron injection layer 114 was formed of LiF having a thickness of 1 nm. The cathode 116 was formed of aluminum (Al) having a thickness of 120 nm.

Voltages and lifetimes of the organic electroluminescent devices were measured. The measured values are shown in the following Table 1.

TABLE 1

|  | Voltage (V) | Luminescence lifetime (Hour) |
| --- | --- | --- |
| Embodiment 1 | 6.5 | 2,850 |
| Comparison Example 1 | 7.5 | 1,600 |
| Comparison Example 2 | 7.0 | 1,250 |
| Comparison Example 3 | 8.1 | 1,200 |

As may be seen in Table 1, the driving voltage of the organic electroluminescent device including the compound of Embodiment 1 was lower than those of the organic electroluminescent devices including the compounds of Comparison Examples 1 to 3. In addition, the luminescence lifetime of the organic electroluminescent device including the compound of Embodiment 1 was considerably longer than those of the organic electroluminescent devices including the compounds of Comparison Examples 1 to 3. Comparison Example 3 is a general compound. Comparison Example 1 has an aryl amine skeleton or core and includes a carbazole moiety, like Embodiment 1, but has a structure including a dibenzothiophene instead of a moiety including a triazine group. A resistance property of the Comparison Example 1 to electrons may be lower than that of Embodiment 1.

Comparison Example 2 is an amine derivative having a triazine group, like Embodiment 1. However, Comparison Example 2 does not have the same aryl amine skeleton or core as Embodiment 1. A carrier transporting property of Comparison Example 2 may be lower than that of Embodiment 1.

By way of summation and review, high-efficiency and long-life organic EL devices may be applied to display apparatuses. Normalization, stability, and durability of the hole transport layer have been considered in an effort to realize the high-efficiency and long-life organic EL devices. Aromatic amine-based compounds and indolocarbazole derivatives have been considered as a hole transport material used for the hole transport layer.

To help increase performance and lifetime of the organic EL device, charge-transporting performance of the hole transport layer and a resistance property of the hole transport layer with respect to electrons invading the hole transport layer may be improved.

The embodiments may provide an aryl amine derivative having high efficiency and long lifetime.

As described above, the aryl amine derivative according to an embodiment may help realize a long lifetime of the organic electroluminescent device in a region of a blue color to a blue-green color. In other organic electroluminescent devices, electrons that are not recombined with holes in an interface region between a light-emitting layer and a hole transport layer may be injected into the hole transport layer. The electrons may damage the hole transport material and may deteriorate the organic electroluminescent device. The aryl amine derivative according to an embodiment may include an azine moiety or derivative, so stability of the hole transport material with respect to electrons may be improved. As a result, it is possible to inhibit deterioration of the organic electroluminescent device (which could be caused by electrons invading the hole transport layer) and to improve the lifetime of the organic electroluminescent device.

The embodiments may provide the high-efficiency and long-lifetime aryl amine derivative, and an organic electroluminescent device using the aryl amine derivative as the hole transport material.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An aryl amine represented by the following Chemical Formula 1,

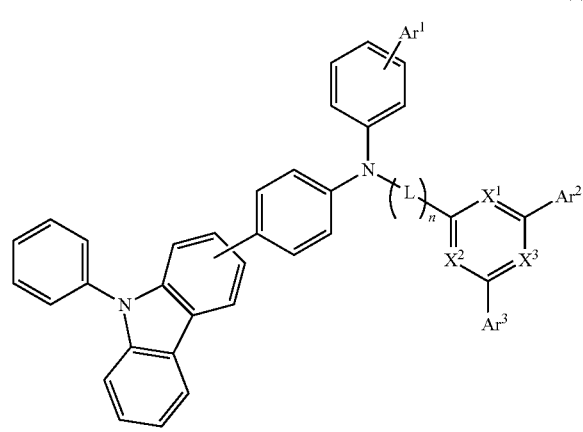

(1)

wherein, in Chemical Formula 1:

$Ar^1$, $Ar^2$, and $Ar^3$ are each independently a substitutable aryl group or a substitutable heteroaryl group, L is a single bond, a substitutable C6 to C25 arylene group, or a substitutable C5 to C25 heteroarylene group, n is an integer of 1 to 3, wherein, when L is the single bond, n is 1, $X^1$, $X^2$, and $X^3$ are each independently a carbon atom or a nitrogen atom, provided that at least one of $X^1$, $X^2$, or $X^3$ is a nitrogen atom.

2. The aryl amine derivative as claimed in claim 1, wherein $X^1$, $X^2$, and $X^3$ are nitrogen atoms.

3. The aryl amine as claimed in claim 2, wherein $Ar^2$ and $Ar^3$ are different from each other.

4. The aryl amine as claimed in claim 1, wherein $Ar^2$ and $Ar^3$ are different from each other.

5. An organic electroluminescent device, comprising a hole transport layer, the hole transport layer including an aryl amine represented by the following Chemical Formula 1,

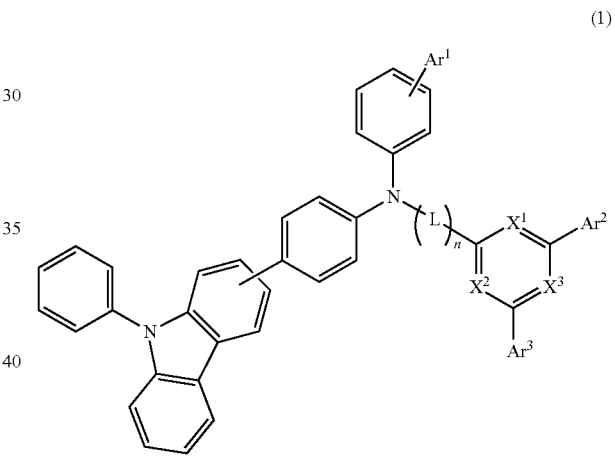

(1)

wherein, in Chemical Formula 1:

$Ar^1$, $Ar^2$, and $Ar^3$ are each independently a substitutable aryl group or a substitutable heteroaryl group, L is a single bond, a substitutable C6 to C25 arylene group, or a substitutable C5 to C25 heteroarylene group, n is an integer of 1 to 3, wherein, when L is the single bond, n is 1, $X^1$, $X^2$, and $X^3$ are each independently a carbon atom or a nitrogen atom, provided that at least one of $X^1$, $X^2$, or $X^3$ is a nitrogen atom.

6. The organic electroluminescent device as claimed in claim 5, wherein $X^1$, $X^2$, and $X^3$ are nitrogen atoms.

7. The organic electroluminescent device as claimed in claim 5, wherein $Ar^2$ and $Ar^2$ are different from each other.

* * * * *